US005663065A

United States Patent [19]

Frey et al.

[11] Patent Number: 5,663,065

[45] Date of Patent: *Sep. 2, 1997

[54] DNA ENCODING INFECTIOUS RUBELLA VIRUS

[75] Inventors: Teryl K. Frey, Atlanta; Geraldina Dominguez, Tucker; Chin-Yen Wang, Roswell, all of Ga.

[73] Assignee: Georgia State University Research Foundation, Inc., Atlanta, Ga.

[ * ] Notice: The term of this patent shall not extend beyond the expiration date of Pat. No. 5,439,814.

[21] Appl. No.: 459,041

[22] Filed: Jun. 2, 1995

Related U.S. Application Data

[63] Continuation-in-part of Ser. No. 93,453, Jul. 19, 1993, Pat. No. 5,439,814, which is a continuation of Ser. No. 722,334, Jun. 28, 1991, abandoned.

[51] Int. Cl.$^6$ .............................. C12N 15/00; C12N 7/00; C12N 15/40; C12N 15/63

[52] U.S. Cl. ....................................... 435/172.3; 536/23.72; 435/235.1; 435/320.1

[58] Field of Search ...................... 536/23.72; 435/320.1, 435/235.1, 172.3, 69.3; 424/219.1

[56] References Cited

U.S. PATENT DOCUMENTS 5,439,814 8/1995 Frey et al. ........................... 435/172.3

OTHER PUBLICATIONS

Mauracher, C.A. et al. Journal of Immunology, vol. 151, pp. 2041–2049 1993.

Hobman, T.C. et al. Virology, vol. 202, pp. 574–585 1994.

Zheng, D. et al. Gene, vol. 82, pp. 343–349 1988.

Frey, T. et al. Journal of Infectious Diseases, vol. 168, pp. 854–864 1993.

Geiger, R. et al. Journal of Medical Virology, vol. 47, pp. 442–444 1995.

Chantler, J.K. et al. Intervirology, vol. 36, pp. 225–236 (abstract only) 1993.

Frenkel, L.M. et al. Arch. Pediatr. Adolesc. Med., vol. 148, pp. 57–60 (abstract only) 1994.

Mitchell, L. A. e tal. Arch. Intern. Med., vol. 153, pp. 2268–2274 (abstract only) 1993.

Ahlquist et al., *J. Mol. Biol.* 172:369–383 (1984).

Ahlquist et al., *Mol. Cell.* Biol. 4: 2876–2882 (1984).

Ahlquist et al., *Proc. Nat'l Acad. Sci.* USA 91: 7066–7070 (1984).

Ballart et al., *EMBOJ* 10(11):3558 (1991).

Callahan et al., *Proc. Nat'l. Acad. Sci.* USA 82: 732–736 (1985).

Clark et al., *Nucleic Acids Res.* 15:3041–3057 (1987).

Cotlier et al., *Nature* 217: 38–40 (1968).

Cunningham et al., *J. Infect. Dis.* 151:638–645 (1985).

Davis et al., *Virology* 171: 189–204 (1989).

Dominguez et al., *Virology* 177: 224–238 (1990).

Frey et al., *Gene* 62: 85–99 (1988).

Frey et al., *Virol.* 168: 191–194 (1989).

Frey et al., *Virology* 154: 228–232 (1986).

Green et al., *J. Virol.* 57: 893–898 (1986).

Hovi et al., *Virology* 42: 1–8 (1970).

Kono et al., *The Lancet* :343–347 (Feb. 15, 1969).

London et al., *Nature* 226: 172–173 (1970).

London et al., *Symp. Series Immunobiol. Standard.* 11: 121–124 (1969).

Mizutan et al., *J. Virol.* 56: 628–632 (1985).

Nakhasi et al., *J. Biol. Chem.* 261: 16616–16621 (1986).

Niesters et al., *J. Virol.* 64: 4162–4168 (1990).

Oh et al., *J. Mol. Biol.* 168:1–15 (1983).

Oker–blom et al., *J. Virol.* 46: 964–973 (1983).

Oker–Blom, *J. Virol.* 51: 354–358 (1984).

Rice et al., *Virology* 61: 3809–3819 (1987).

Takkinen et al., *J. gen. Virol.* 69: 603–612 (1988).

Vidgren et al., *J. Gen. Virol.* 68: 2347–2357 (1987).

Wang et al., *J. Virol.* 68(6): 3550–3557 (1994).

Waxham et al., *Virology* 126: 194–203 (1983).

Waxham et al., *Virology* 143: 153–165 (1985).

Weibel et al., *Proc. Soc. Exp. Biol. Med.* 165: 44–45 (1980).

Zheng et al., *Gene* 82: 343–349 (1989).

*Primary Examiner*—Mary E. Mosher

*Attorney, Agent, or Firm*—Jones & Askew

[57] ABSTRACT

An infectious rubella virus cDNA clone and entire rubella virus genomic RNA sequence. Non-pathogenic mutants of this clone are useful as vaccines to vaccinate humans, including pregnant or older women, with decreased risk of causing fetal infection, autoimmune disease or neurological symptoms.

4 Claims, 6 Drawing Sheets

Page 1 of 3

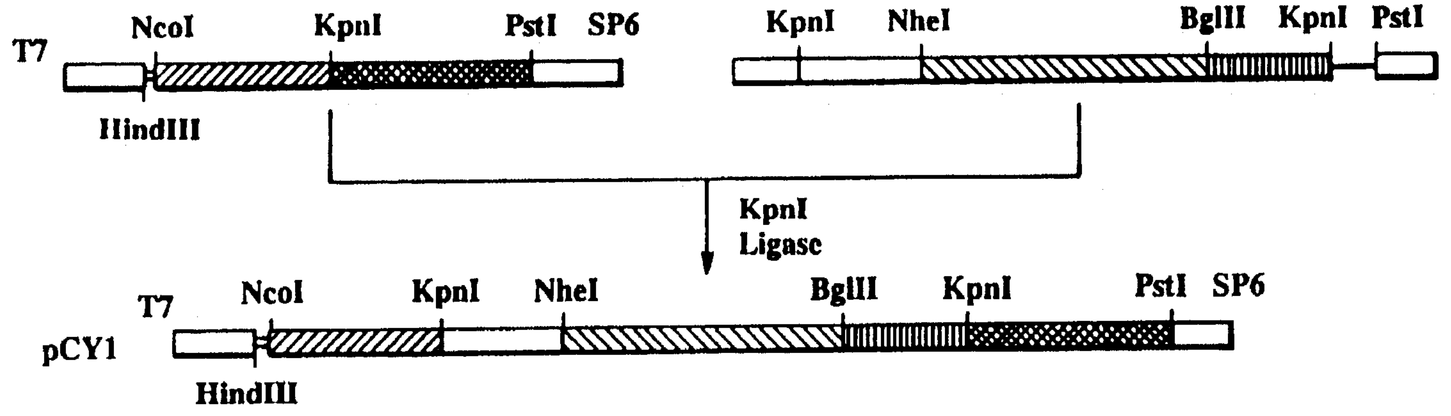

Mutagenic oligo

SpeI HindIII

5' AGCTACTAGTCTAAGCTTTCGGACCTCGCTTAGGACTCCCATTCC 3'
TGATCAGATTCGAAAGCCTGGAGCGAATCCTGAGGGTAAGGGTAC

FIG. 2A

Page 2 of 3

5' end modification :
Primer 1 TTCGAAGCTTATTTAGGTCACACTATA
GCATGGAAGCTATCGGACCTC
Primer 2 TGGTCTCTTACCCAACT
AAAA RUB RNA
Primer 2

3' end modification :
Primer 3 GATGCATCCCTATAGTGAGTCGTATTAG
Primer 4 AATTCTAATACAACTCACTATAGGGATG
CATCTGCA
Primer 5 AATGCCCGAGTGGATCCA
Primer 6 ACGTGCATGCCTGCAGTTTTTTTTTTTT
TTTTTTTT Page 3 of 3

DNA ENCODING INFECTIOUS RUBELLA VIRUS

CROSS-REFERENCE TO RELATED APPLICATIONS

This is a continuation-in-part of U.S. patent application Ser. No. 08/093,453, filed on Jul. 19, 1993, now U.S. Pat. No. 5,439,814 which is a continuation of U.S. patent application Ser. No. 07/722,334, filed on Jun. 28, 1991, now abandoned.

The U.S. Government has rights in this invention arising out of National Institutes of Health (NIAID) grant numbers AI21389 and AI00923.

The present invention relates to the field of molecular virology and more particularly to construction of a modified recombinant rubella virus vaccine.

BACKGROUND OF THE INVENTION

Rubella virus is a major human pathogen. Infection with rubella virus can cause serious birth defects and chronic disease. There was a mini-epidemic of both rubella and congenital rubella syndrome in the United States between 1989 and 1991.

Rubella was first described in the eighteenth century in Germany. The symptoms of a rash and mild fever were similar to those of measles, so the disease was given the name German measles. The name "rubella" was coined in 1814 when physicians realized that the disease was unique and was not merely a variant of scarlatina (scarlet fever) or rubeola (measles).

Rubella is a relatively harmless disease in young children. However, during the first trimester of pregnancy, rubella virus infection can cause fetal death. If the fetus survives, it may be born deaf or have cataracts, cardiac abnormalities, microcephaly, motor deficits or other congenital anomalies. The infant may also be born with thrombocytopenic purpura, hepatosplenomegaly, icterus, anemia, and low birth weight. The presence of one or more of these defects has been termed "congenital rubella syndrome" or CRS.

The rubella virus was isolated in 1962 at the beginning of a worldwide rubella epidemic which lasted from 1962 to 1965. This epidemic peaked in the United States in 1964, resulting in the birth of approximately 20,000 infants exhibiting congenital rubella syndrome.

Scientists began development of an effective vaccine against the rubella virus during the rubella epidemic. Effective attenuated vaccines became available in the late 1960's and are still used today. These attenuated vaccines are live viruses that have been passaged to reduce their virulence. Attenuated vaccines produce immunity, but can cause disease. Protection is believed to persist for at least 15 years after inoculation with the attenuated rubella vaccine.

Various vaccination schedules have been set up in different parts of the world to eliminate rubella infection, especially of the human fetus. The rubella immunization program established in Great Britain requires vaccination of all girls between the ages of 10 and 14. The United States immunization program vaccinates infants at approximately 15 months and requires a certificate of vaccination prior to attending school. The United States program is designed to eradicate the disease among the population that is most responsible for transmission of rubella, whereas the program of Great Britain seeks to achieve complete protection for those at risk for pregnancy. One disadvantage to the United States program is that protection against rubella may dissipate at the very time when immunity is most needed, namely, during the child-bearing years.

Vaccination of women of child-bearing age having undetectable antibody titers is recommended in both the United States and Great Britain. However, there are several risks to this procedure. First, there is a risk that these women may be pregnant and not be aware of their pregnancy, or they may become pregnant within a few months following immunization. Vaccination against rubella is contraindicated in pregnant women because the live virus in the vaccine can cross the placenta and infect the fetus. Pregnant women who have not previously been infected with the rubella virus or who have not been vaccinated prior to becoming pregnant are advised to refrain from becoming vaccinated during their pregnancy. These women are therefore at risk for contracting rubella by coming in contact with infectious persons, including those recently vaccinated with the attenuated vaccine.

Vaccination of older women has been associated with chronic arthritis and neurological symptoms. Scientists believe that these symptoms may be due to the persistent nature of the attenuated rubella virus in the currently available vaccines. Rubella virus is the sole member of the rubivirus genus of the Togavirus family. Compared to other viruses, very little is known about the molecular biology of the rubella virus. The rubella virion consists of single-stranded RNA encapsidated in an icosahedral nucleocapsid surrounded by a lipid envelope. Multiple copies of a viral protein, designated the C protein (MW=32,000–38,000 daltons), make up the nucleocapsid. Two types of viral glycoprotein, designated E1 and E2 (MW=53,000–58,000 daltons and 42,000–48,000 daltons, respectively), are embedded in the envelope, as reported by Waxham, M. N. and Wolinsky, J. S., *Virology* 126:194–203 (1983). The E2 glycoprotein has been further subdivided into two subgroups, designated E2a and E2b, by their ability to migrate differently when resolved by polyacrylamide gel electrophoresis, as described by Oker-Blom, C., et at., *J. Virol.* 46:964–973 (1983). E1 is the viral hemagglutinin. Neutralizing epitopes have been found on both E1 and E2 by Waxham, M. N. and Wolinsky, J. S., *Virology* 143:153–165 (1985) and Green, K. Y., and Dorsett, P. H., *J. Virol.*, 57:893–898 (1986).

The rubella virus genomic RNA is of positive polarity and is capped and polyadenylated. In infected cells, a second positive polarity RNA strand is synthesized to serve as messenger RNA for translation of structural proteins. This second strand is the first 3327 nucleotides beginning from the 3' end of the genomic RNA. The structural proteins are proteolytically processed from a polyprotein precursor during translation. The order of these proteins in the polyprotein is $NH_2$—C—E2–E1—COOH, as reported by Oker-Blom, C., et al. (1983); Oker-Blom, C. *J. Virol.* 51:354–358 (1984).

Recombinant vaccines are based on live microorganisms which have been genetically manipulated so that they are not pathogenic, but result in immunity against the virulent organism. Recombinant vaccines can only cause disease if a rare genetic mutation or recombinant event occurs which allows the microorganism to revert to wild type. A recombinant vaccine is generally safer and more effective than an attenuated vaccine because the engineered mutations remove or inactivate only specific portions of the genome, whereas attenuated vaccines contain random mutations. In order to develop a recombinant vaccine, one must first have the nucleic acid sequence of the entire viral genome, including both the information required for infection and at least limited replication of the virus, and for antigenicity. Once the entire sequence has been determined, a cDNA clone can be produced that is infectious and can be modified to be non-virulent.

An infectious cDNA clone is a complete DNA copy of an RNA virus genome contained in a vector, such as a plasmid, from which RNA transcripts of the genome can be synthesized in vitro. In the case of positive-polarity RNA viruses such as rubella, such transcripts are infectious when transfected into cells. The development of an infectious clone is a landmark event in the molecular biology of any RNA virus. Although Rice et al., *Virology* 61:3809–3819 (1987), have recently developed an infectious clone for the Sindbis virus, no infectious clones have yet been developed for the rubella virus.

Scientists have made many attempts over the past few years to sequence the rubella virus genomic RNA, but have only succeeded in sequencing the genes for the structural proteins and a small section of the 3' end of the non-structural virus genome. Frey, et al., *Virology* 154:228–232 (1986), reported the sequence of the region of the rubella virus genome encoding the glycoprotein E1. These results were confirmed by Nakhasi, et at., *J. Biol. Chem.* 261:16616–16621 (1986). Clark, et al., *Nucleic Acids Res.* 15:3041–3057 (1987), reported the sequence of the subgenomic mRNA of the rubella virus encoding the structural proteins E1, E2 and C. Vidgren, et at., *J. Gen. Virol.* 68:2347–2357 (1987), reported the sequencing of the genes for glycoproteins E1 and E2. Takkinen, et al., *J. Gen Virol.* 69:603–612 (1988), described the isolation of the sequence encoding the virus capsid protein C. Frey and Marr, *Gene* 62:85–99 (1988), described the sequence of the structural proteins C and E2 as well as the carboxyl terminus of a portion of the non-structural virus genome.

It is clear that there remains a strong need to have the complete sequence of the rubella virus RNA genome. Once the sequence is known, an infectious cDNA clone of the rubella virus genome can be developed and used to design a rubella vaccine that can be safely administered to pregnant and older women without risk of birth defects, autoimmune disease or neurologic symptoms.

SUMMARY OF THE INVENTION

The present invention is the entire sequence of the rubella virus genome including the 5250 nucleotides at the 5' terminus encoding non-structural proteins which are critical to infection by the virus, an infectious cDNA clone containing the sequence, and recombinant vaccines against the rubella virus based on the recombinant clone in a pharmaceutically acceptable carrier for administration to a patient.

The recombinant rubella vaccine is prepared by transcribing RNA from a plasmid containing a non-pathogenic, infectious cDNA clone, infecting culture cells with the RNA, replicating the RNA to produce recombinant virus, and combining the virus with a pharmaceutically acceptable carrier, which is then administered to people to be vaccinated, using a schedule and amount demonstrated to be efficacious with other attenuated rubella vaccines. In a second embodiment of this vaccine, the vaccine contains immunogenic epitopes against other viruses, providing a means for immunizing against more than one virus in a single vaccine.

It is therefore an object of the present invention to provide the entire sequence of the rubella virus genomic RNA.

It is a further object of the present invention to provide an infectious cDNA clone of the rubella virus genomic RNA.

It is a further object of the present invention to provide a rubella virus nucleic acid probe.

It is a still further object of the present invention to provide a recombinant attenuated rubella vaccine derived from a non-pathogenic infectious cDNA clone that can be safely administered to pregnant and older women.

It is another object of the present invention to provide a combined recombinant attenuated vaccine effective against rubella and one or more other viruses.

DETAILED DESCRIPTION OF THE INVENTION

Figure 1:
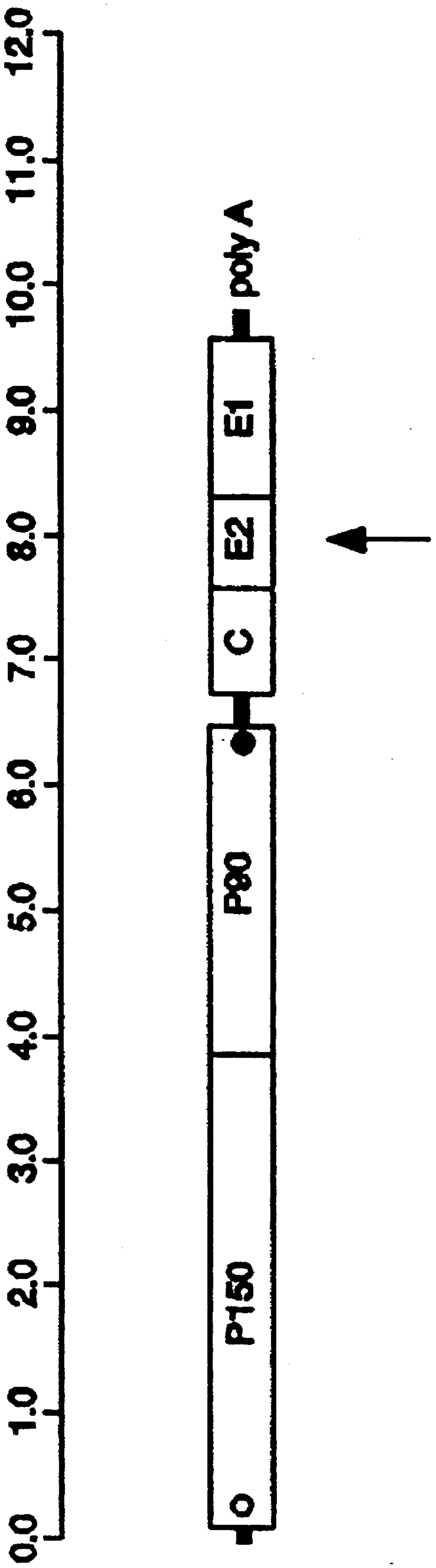
FIG. 1 is a schematic representation of the rubella virus genome with arrows showing a region in which the sequence can be modified to decrease virulence without loss of infectivity and immunogenicity.

The entire rubella virus RNA genome has been sequenced, including the 5250 nucleotides at the 5' terminus encoding non-structural proteins which are critical to infection by the virus, and an infectious cDNA clone has been constructed. Mutations made in one or more regions of the cDNA clone render the resultant RNA virus non-pathogenic. The non-pathogenic RNA virus is combined with a pharmaceutically acceptable carrier to form a vaccine.

As shown below in SEQ ID NO. 1, the wild-type rubella virus genomic RNA is 9759 nucleotides in length, excluding the poly(A) tail, and has a high guanosine plus cytosine ratio (G+C) content (69.5%). The rubella virus genomic RNA contains two long open reading frames, a 5' proximal open reading frame of 6345 nucleotides which most likely encodes the nonstructural proteins and a 3' proximal open reading frame of 3189 nucleotides which encodes the structural proteins. Within the 5' proximal open reading frame are two amino acid motifs commonly associated with replicase and helicase function, indicating the importance of this open reading frame in viral RNA replication. A stretch of 46 nucleotides is located 224 nucleotides from the 5' end of the genome (denoted by an open circle in FIG. 1). This sequence is similar to a sequence conserved among alphaviruses which is believed to play a role in RNA replication. The rubella genome also contains a 20 nucleotide stretch 20 nucleotides upstream from the subgenomic RNA start site which shares homology with a conserved alphavirus sequence (denoted by a closed circle in FIG. 1). This sequence is believed to be the subgenomic RNA promoter.

The predicted amino acid sequence of the rubella virus genome can be determined from the nucleotide sequence by well known methods. The 5'-proximal open reading frame begins at nucleotide 41 and terminates at position 6385 with a UAA codon followed 24 nucleotides downstream by a second inframe UAA codon. The 5'-proximal open reading frame is 6345 nucleotides in length and encodes a 2115-amino acid polypeptide. The 3'-proximal open reading frame begins at nucleotide 6509 and ends at nucleotide 9698. It is 3189 nucleotide in length and encodes a polypeptide of 1063 amino acids which is cleaved into at least three structural proteins, C, E1 and E2, as discussed above.

The two open reading frames are shown in FIG. 1. The letters C, E2 and E1 represent the genes for the structural capsid, envelope 2 and envelope 1 glycoproteins respectively. The small black region at the 5' end of the genome represents a 5' cap and 40 nucleotide untranslated region while the small black region at the 3' end represents a 58 nucleotide untranslated region followed by the poly(A) tail.

The present invention will be further described with reference to the following description of the isolation and characterization of the RNA sequence and the infectious cDNA clone for the rubella virus RNA genome. The teachings of the references describing in detail the methods used in the isolation, characterization, and modification of the RNA sequences are specifically incorporated herein by reference. In addition to being useful for the preparation of a rubella virus vaccine, the nucleotide sequence is useful as a nucleic acid probe for the detection of rubella virus.

RNA isolation:

Virion RNA from the Therien strain of rubella virus was isolated by phenol-chloroform extraction of virions purified as described by Waxham, M. N. and Wolinsky, J. S., *Virology* 126:194–203 (1983). Intracellular RNA was extracted from infected Vero cells (m.o.i.=0.1) at 72 hours postinfection as described by Frey, T. K., *Virology*, 154:228–232 (1986). The extracted RNA was chromatographed over oligo(dT) cellulose. After ethanol precipitation, the poly(A)+ fraction was dissolved in 90% DMSO and heated at 55° C. for five minutes to denature double-stranded RNA replicative forms and intermediates which bind to oligo(dT) cellulose. The DMSO-denatured RNA was ethanol precipitated twice and dissolved in 0.01M Tris (pH 8.0), 0.001M EDTA.

Derivation and sequencing of cDNA clones:

Virion RNA was used as the template for first-strand cDNA synthesis primed with random deoxyhexamers (Pharmacia Fine Chemicals, Piscataway, N.J.) as described by Rice, C. M., et al., *Science* 229:726–733 (1985). Second-strand DNA synthesis, deoxycytidine (dC) tailing of the double-stranded cDNA with terminal transferase, annealing of dC-tailed cDNA with dG-tailed pUC 9, and transformations were done as described by Frey, et al., *Virology* 154:228–232 (1986) with the following modifications: double-stranded cDNA was chromatographed on a Sepharose™ CL-4B column (Pharmacia) to eliminate cDNAs less than 700 nucleotides in length, as described by Eschenfeldt, W. H. and Berger, S. L., Purification of large double-stranded cDNA fragments. In METHODS IN ENZYMOLOGY, S. L. Berger and A. R. Kimmel, Eds., Vol. 152:335–337 Academic Press, New York (1987), the teachings of which are incorporated herein, and transformed using competent DH5-α cells (Bethesda Research Labs, Bethesda, Md.).

Colonies with cDNA clones containing sequences overlapping the 3'-terminal 4508 nucleotides of the genome, described by Frey, T. K. and Marr, L. D., *Gene* 62:85–99 (1988), were identified by colony blot hybridization using as probes $^{32}$P-labeled restriction fragments and oligonucleotides from the 5' end of this sequence. This set of cDNA clones was restriction mapped and a restriction fragment from the 5' end of this set of clones was used as a probe to isolate new overlapping clones. Eighteen clones were identified and mapped which covered the region between 4500 nucleotides from the 3' end of the genome and the 5' end of the genome.

Sequencing strategy:

The cDNA inserts from eight clones representative of the region to be sequenced were subcloned into M13 for sequencing. Subcloning by use of convenient restriction sites, shotgun cloning of sonicated DNA, described by Bankier, A. T. and Barrell, B. G., *Nucleic Acid Biochem.* *B*508:1–34 (1983), and exonuclease III digestion to produce directional deletions, as described by Henikoff, S., *Gene* 28:351–359 (1984), the teachings of which are incorporated herein, were all employed. Several gaps which remained were sequenced using synthetic oligonucleotide primers on the appropriate templates. Oligonucleotides were synthesized using an Applied Biosystems Model 381A DNA Synthesizer. All sequencing was done by dideoxy sequencing, as described by Sanger, F., et al., *Proc. Natl. Acad. Sci. USA* 74:5463–5467 (1977), using the procedure recommended by Sequenase Version 2.0 kit (United States Biochemical Corp., Cleveland, Ohio) with [$^{32}$S]dATP label and 7-deaza-dGTP in place of dGTP.

Primer extension and dideoxy sequencing from an RNA template were both performed on poly(A)+RNA from rubella-infected cells using as a primer a 5'-$^{32}$P-labeled oligonucleotide with the sequence dTGGTCTCTTACCCAACT (SEQ ID NO. 2), which is complementary to nucleotides 101 to 117 of the genomic RNA. The primer extension reaction was done as described by Frey, T. K., et al., *Virology* 168:191–194 (1989), while RNA sequencing was done by dideoxy sequencing modified for an RNA template using the method of Rico-Hesse, R., et al., *Virology* 160:311–322 (1987), and Zimmern, D. and Kaesberg, P., *Proc. Natl. Acad. Sci. USA* 75:4257–4261 (1978).

Computer analysis:

The analysis of the sequence was performed on the Centers for Disease Control VAX using the University of Wisconsin GCP package, designed by Devereux, J., et al., *Nucl. Acids. Res.* 12:387–395 (1984).

Isolation of infectious cDNA clone:

A cDNA copy of the complete rubella genome RNA was assembled in a plasmid with an SP6 RNA polymerase promoter immediately adjacent to the 5' end of the cDNA. RNA transcripts from the construct were produced. As a stringent assay was employed to ascertain that the transcripts, which appeared to be full length by agarose gel electrophoresis, were indeed full length. Northern blot analysis was done on the transcripts using as a probe a radiolabeled oligonucleotide complementary to the 3' terminal 30 nucleotides of the rubella genome. Transcripts from the construct hybridized with the 3' terminal probe.

The following strategy was used to isolate an infectious clone, based on the nucleotide sequence. However, it would have been very difficult to make the clone from the sequence, without the cDNAs to combine to make the clone, and the addition of two nucleotides at the 5' end.

Figure 2A:
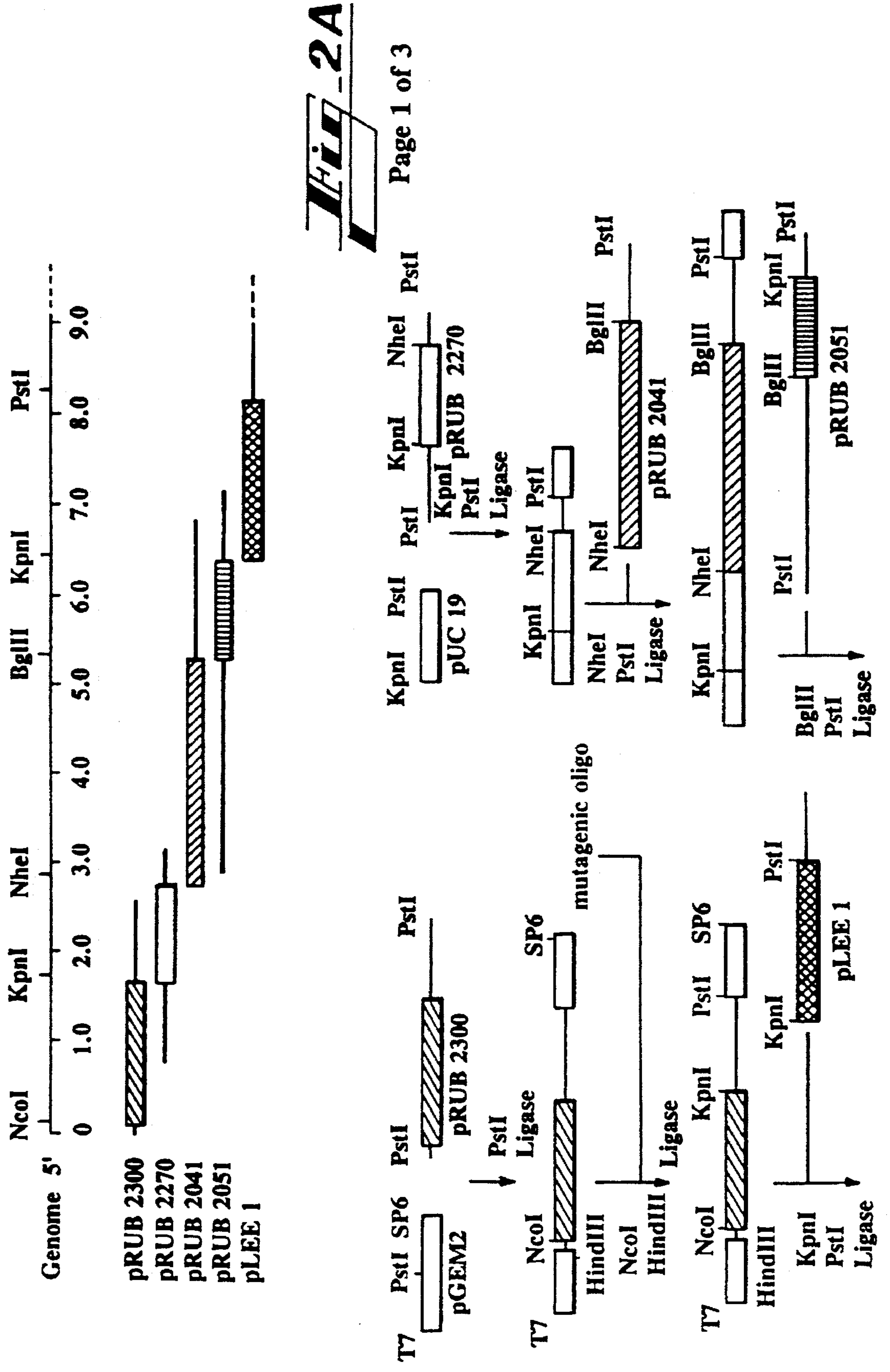
FIG. 2*a* is a schematic of the construction strategy of a non-infectious total genomic construct of the rubella virus, Robo 1, showing the mutagenic oligonucleotide and primers 1–6
Figure 2A:
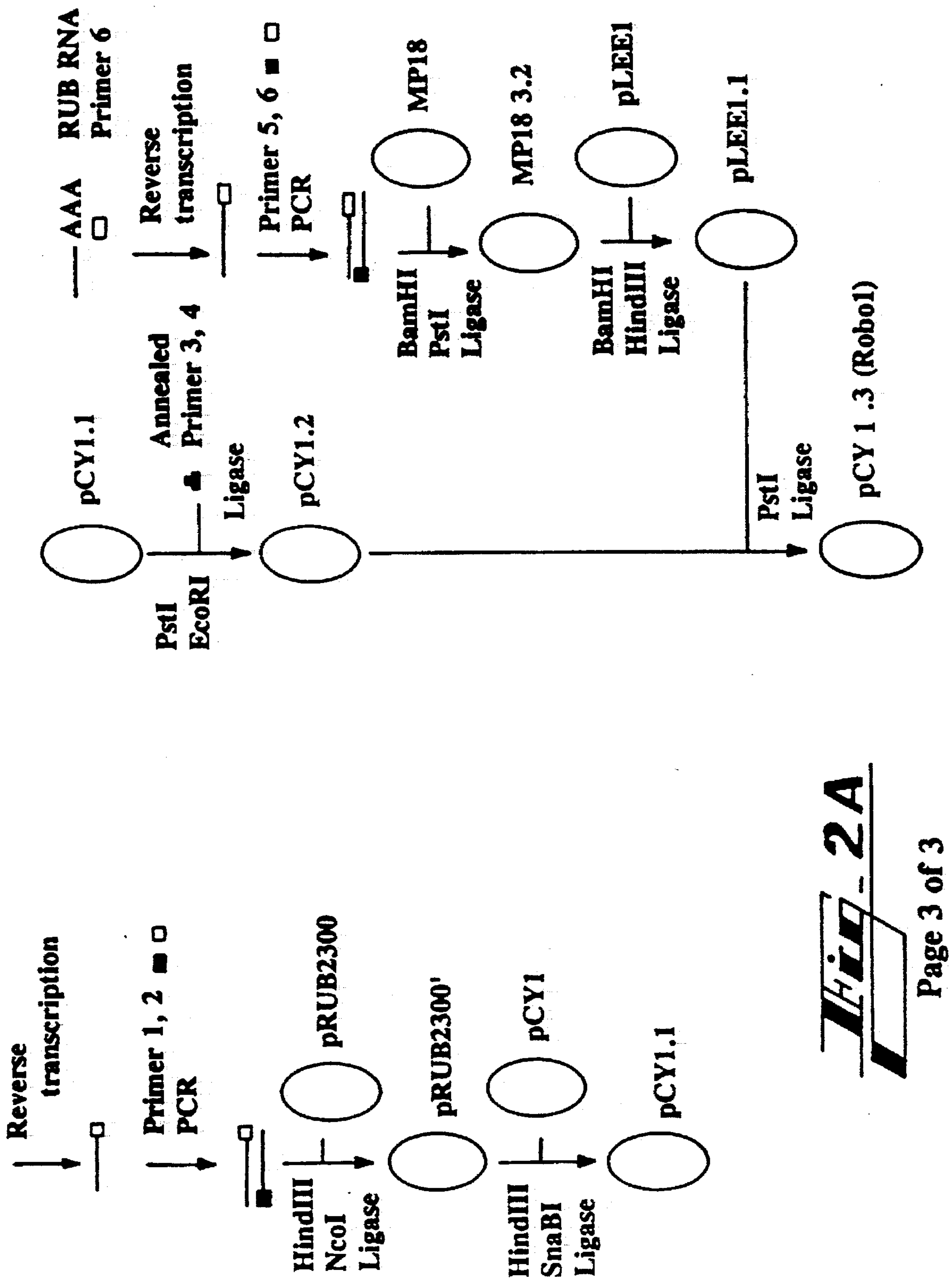
Figure 2B:
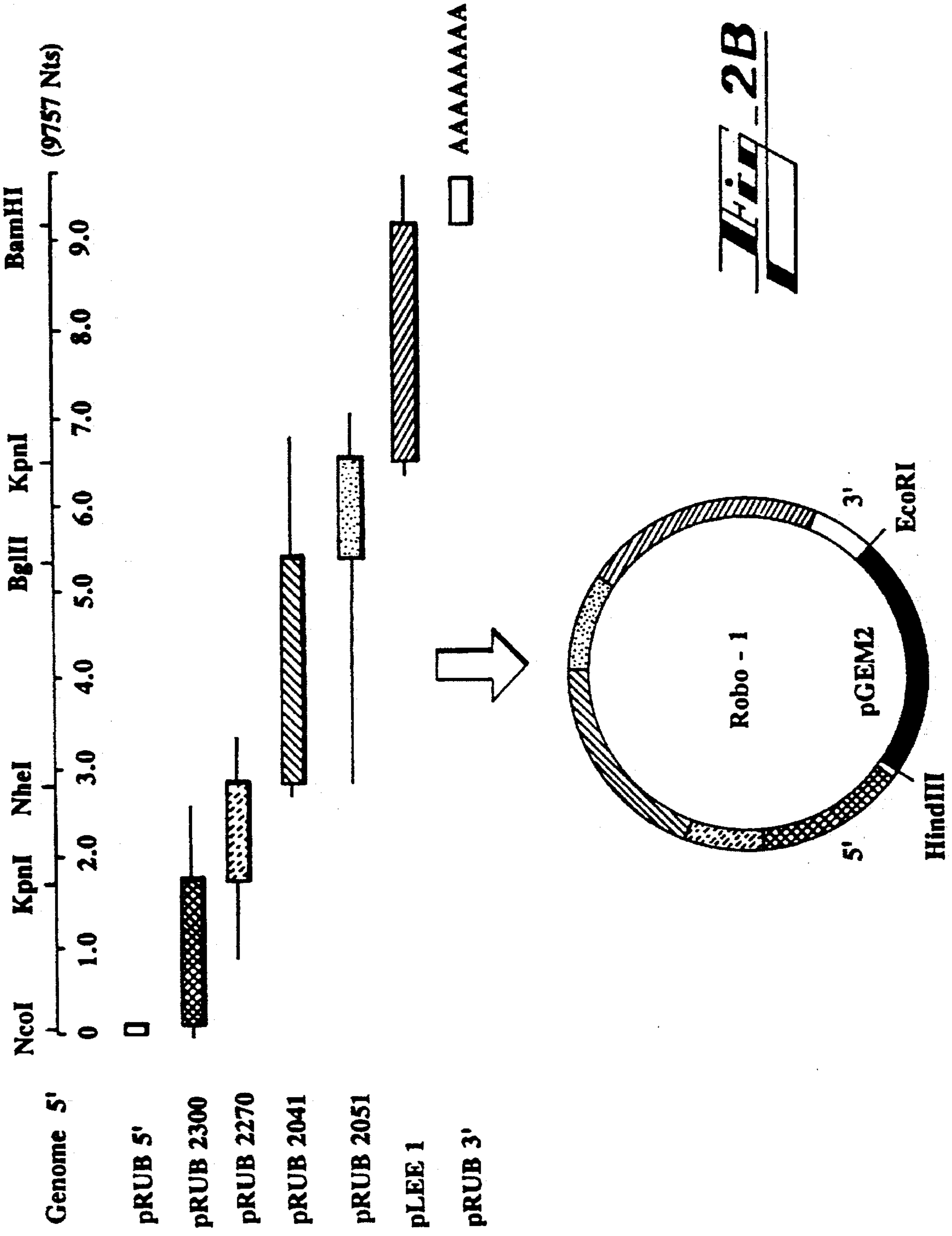
FIG. 2*b* is a schematic of the relative locations of each cDNA derived from the clones and the oligonucleotides used to modify the 3' and 5' ends.

The strategy and resulting construct are shown in FIGS. 2*a* and 2*b*. FIG. 2*a* provides the sequences of the mutagenic oligonucleotide (SEQ ID NO. 3) and Primers 1–6 (SEQ ID NOS. 4–9). Four overlapping cDNAs derived as described above for sequencing of the 5248 5' terminal nucleotides, a construct pLEE 1 which contained the structural protein coding regions derived as described by Frey, et al., (1986) and Frey and Marr (1988), the teachings of which are specifically incorporated herein, 40 nucleotides at the 5' end synthesized with a DNA synthesizer (Applied Biosystems) and approximately 50 nucleotides at the 3' end synthesized with a DNA synthesizer, were combined to form a construct Robo 1. Transcripts of this construct were not infectious. The sequence of the construct Robo 1(SEQ ID NO. 10 ) is shown in FIG. 3.

Figure 3:
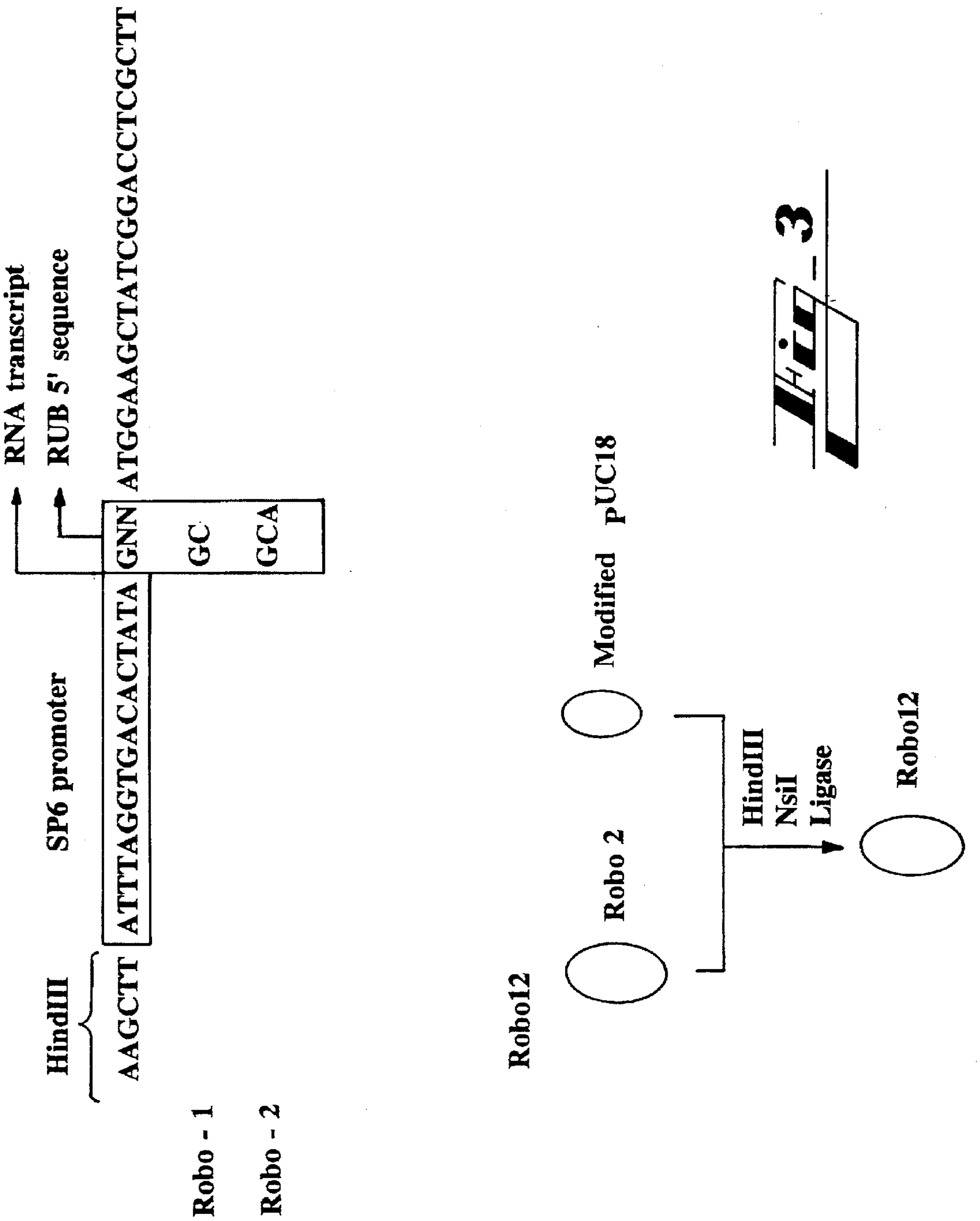
FIG. 3 is a schematic of modifications to the construct Robo1 of FIG. 2 to produce an infectious clone, Robo102, showing a portion of the 5' end of the sequence.

As shown in FIG. 3, two subsequent modifications, adding two nucleotides, C and A, at the 5' end and removing one SP6 promoter at the 3' end of the construct (leaving the SP6 promoter immediately adjacent the 5' end) by cleaving with restriction enzymes to remove the construct in pGEM2, which contains an SP6 promoter, and inserting the construct into pUC18, yielded Robo12, transcripts of which were infectious. It appears that the addition of the CA at the 5' end was crucial to making an infectious clone. The construct containing these two additional nucleotides is shown in FIG. 3 as Robo 2 (SEQ ID NO. 11). This portion of the sequence had not previously been reported. The construct was subsequently inserted into pC11921 (Lerner, C. G., and Inouye, M., Nucl., Acids Res. 18:4361 (1990)) to obtain enhanced stability, yielding Robo102.

BHK-21 cells obtained from Dr. Charles M. Rice, Department of Microbiology and Immunology, Washington University School of Medicine, St. Louis, Mo., were transfected with the transcripts using lipofectin-mediated transfection techniques described by Rice, C. M., Graloue, A., Galler, R., Chambers, T. J., Transcription of infectious yellow fever RNA from full-length cDNA templates produced by in vitro ligation. *The New Biologist* 1, 285–296 (1989). (BHK-21 cells are available from the American Type Culture Collection. Lipofectin can be purchased from Bethesda Research Laboratories Inc., Gaithersburg, Md.) To detect the production of rubella virus in transfected BHK-21 cells, culture fluid was harvested and used to infect Vero cells obtained from the American Type Culture Collection. Vero cells were cultured at 35° C. under 4% $CO_2$ in Eagle Minimal Essential Medium containing Earle's salts and supplemented with 10% tryptose phosphate and 5% fetal bovine serum. Streptomycin was also added to minimize bacterial contamination.

Rubella virus was recovered from Vero cells infected with culture fluid from BHK-21 cells transfected with RNA extracted from virions and with RNA transcribed from the SP6 genomic construct, demonstrating that the cDNA clones were infectious.

Mutagenesis of cDNA clone:

The infectious cDNA clone can be modified in one or more of several ways to render it less virulent, while retaining infectivity and immunogenicity. Most preferably, a mutation or mutations are made to render the virus non-persistent. A non-persistent virus is defined herein as one that becomes non-virulent after the initial infection and development of an immune response but before the onset of arthritis or neurological impairment. As an example, non-persistence can be measured by the absence of viral penetration of synovial fluid.

In the preferred embodiment, a mutation is made in the E2 gene as shown in FIG. 1. Alternatively, a mutation may be make in the E1 gene. Rubella virus is unique among enveloped viruses in that it buds both at intracellular membranes and at the cytoplasmic membrane, as reported by Bardeletti, G., et al., *Intervirology* 11:97–103 (1979). Rubella virus nucleocapsids form in association with membranes at the site of budding. Evidence suggests that the intracellular budding occurs at the endoplasmic reticulum and the Golgi apparatus. During intracellular budding, the rubella virus glycoproteins are retained at both sites for a prolonged period of time, six hours or greater, leading to delayed appearance of viral glycoproteins at the cell surface. It is believed that both E1 and E2 mediate the interaction of the C protein with these intracellular membranes to form intracytoplasmic vacuoles. These vacuoles may allow the rubella virus to persist in the presence of a humoral immune response. Therefore, mutations in the E1 or E2 gene should adversely affect persistence.

A mutation or mutations may also be made to render the rubella virus incapable of binding to or crossing the placenta to infect a fetus. Mutated virus may be tested for this characteristic by infecting placental tissue or placental cells with virus produced from the infectious clone and recovering the virus that fails to bind to these cells. Such viruses are presumed to have lost recognition for the receptor in placental cells. After growing these viruses in regular cell culture, such as Vero cells, the process is repeated to enrich for viruses that do not interact with placental cells. C-DNA can be prepared from these viruses and specific cDNA fragments introduced into the infectious clone. Subsequently, recovered virus can be assayed for placental infection. By correlating the different cDNA fragments introduced into the infectious clones with infection of placental tissue, the exact region of the virus necessary for replication in placentae can be identified. The mutation that abrogates infectivity of placenta can then be incorporated into the vaccine.

A similar strategy may be employed with synovial cells. It is believed that rubella virus causes arthritis by replicating in synovial cells. A mutant that fails to replicate in synovial cells may therefore be less likely to cause arthritis.

The mutations are created using standard recombinant molecular biology techniques known to those skilled in the art such as linker-insertion mutagenesis, site-directed mutagenesis or homologous recombination. These techniques are described by, for example, Maniatis, T., Fritsch, E. F. and Sambrook, J., MOLECULAR CLONING: A LABORATORY MANUAL, (Cold Spring Harbor Laboratory, Cold Spring Harbor, N.Y. 1989).

Production and Screening of modified virus for decreased virulence:

The modified cDNA clone is placed within a vector, preferably a bacterial plasmid such as pUC 19, pGEM, or PBR-322 (all available from Promega Biotec, Madison, Wis.) or pC11921 adjacent to a bacteriophage RNA polymerase promoter sequence such as the SP6 RNA polymerase (Promega Biotec) such that RNA copies of the rubella virus DNA can be synthesized in vitro. The vector is chemically introduced into susceptible culture cells, for example, *E. coli*, for amplification and production of large amounts of the cDNA clone. For use, the purified infectious clone is restricted with a restriction endonuclease such as Nsi 1 (New England Biolabs, Beverly, Mass.) for linearization at the termination of the rubella virus cDNA sequences. The linearized plasmid is then transcribed with an RNA polymerase such as SP6 RNA polymerase, which results in production of RNA transcripts templated from the rubella virus cDNA sequence in the non-pathogenic infectious clone.

When an appropriate amount of the infectious clone RNA transcript is transfected into susceptible cells by transfection procedures known to those skilled in the art, less virulent rubella virus is recovered from the culture fluid within several days incubation. Preferably, an amount ranging from 0.5 to 1.5 micrograms of the infectious clone transcript is transfected into BHK-21 cells by lipofectin-mediated transfection. The identity of the virus recovered from the transfected cells can be confirmed by sequencing a specific region of the infectious clone in which a mutation exists which distinguishes it from the wild-type virus.

The less virulent rubella virus is then combined with a pharmaceutically acceptable carrier to provide a safe, effective rubella virus vaccine. The carrier can be oil, water, saline, phosphate buffer, polyethylene glycol, glycerine, propylene glycol, and combinations thereof, or other vehicles routinely used by the pharmaceutical industry for these purposes. The vaccine is usually provided in lyophilized form and therefore is free of preservatives.

It will be understood by those skilled in the art that modified cDNA for other DNA or RNA viruses could be inserted into the vector in combination with the rubella virus cDNA to make a vaccine effective in immunizing a patient against more than one virus. For example, the modified cDNA of RNA viruses such as hepatitis C or Dengue fever virus could be inserted into the vector to produce a combined recombinant vaccine.

Methods of administration:

The vaccine can be administered by any appropriate route, for example, orally, parenterally, intravenously, intradermally, intramuscularly, subcutaneously, or topically, in liquid or solid form, which results in infection and elicitation of an immune response against the wild-type rubella virus. The vaccine is preferably administered subcutaneously at a concentration range from $10^2$ to $10^4$ $TCID_{50}$/person. (TCID is an abbreviation for tissue culture infectious doses.) Preferably the vaccine is provided to the physician in a lyophilized form, is reconstituted in an appropriate solvent such as deionized water or saline and administered as a single injection.

Modifications and variations of the DNA encoding an infectious rubella virus, method of making a less virulent rubella virus, an improved rubella virus vaccine and methods of use thereof will be obvious to those skilled in the art from the foregoing detailed description of the invention. Such modifications and variations are intended to come within the scope of the appended claims.

We claim:

1. An isolated DNA molecule comprising a nucleotide sequence encoding an infectious rubella virus, which corresponds to the cDNA sequence of SEQ ID NO. 1.

2. The molecule of claim 1 further comprising a vector, wherein the vector enables replication of the nucleotide sequence.

3. The molecule of claim 2 wherein the vector is a bacterial plasmid.

4. A method of producing a rubella virus comprising the steps of:

a. inserting a DNA molecule having the nucleic acid sequence of SEQ ID NO. 1 into a plasmid;

b. transcribing the DNA into linear RNA;

c. transfecting cells with the nucleic acid transcript; and d. recovering rubella virus from the transfected cells.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 9759 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

```
CAATGGAAGC TATCGGACCT CGCTTAGGAC TCCCATTCCC ATGGAGAAAC TCCTAGATGA     60
GGTTCTTGCC CCCGGTGGGC CTTATAACTT AACCGTCGGC AGTTGGGTAA GAGACCACGT    120
CCGATCAATT GTCGAGGGCG CGTGGGAAGT GCGCGATGTT GTTACCGCTG CCCAAAAGCG    180
GGCCATCGTA GCCGTGATAC CCAGACCTGT GTTCACGCAG ATGCAGGTCA GTGATCACCC    240
AGCACTCCAC GCAATTTCGC GGTATACCCG CCGCCATTGG ATCGAGTGGG GCCCTAAAGA    300
AGCCCTACAC GTCCTCATCG ACCCAAGCCC GGGCCTGCTC CGCGAGGTCG CTCGCGTTGA    360
GCGCCGCTGG GTCGCACTGT GCCTCCACAG GACGGCACGC AAACTCGCCA CCGCCCTGGC    420
CGAGACGGCC AGCGAGGCGT GGCACGCTGA CTACGTGTGC GCGCTGCGTG GCGCACCGAG    480
CGGCCCCTTC TACGTCCACC CTGAGGACGT CCCGCACGGC GGTCGCGCCG TGGCGGACAG    540
ATGCTTGCTC TACTACACAC CCATGCAGAT GTGCGAGCTG ATGCGTACCA TTGACGCCAC    600
CCTGCTCGTG GCGGTTGACT TGTGGCCGGT CGCCCTTGCG GCCCACGTCG GCGACGACTG    660
GGACGACCTG GGCATTGCCT GGCATCTCGA CCATGACGGC GGTTGCCCCG CCGATTGCCG    720
CGGAGCCGGC GCTGGGCCCA CGCCCGGCTA CACCCGCCCC TGCACCACAC GCATCTACCA    780
AGTCCTGCCG GACACCGCCC ACCCCGGGCG CCTCTACCGG TGCGGGCCCC GCCTGTGGAC    840
GCGCGATTGC GCCGTGGCCG AACTCTCATG GGAGGTTGCC CAACACTGCG GGCACCAGGC    900
GCGCGTGCGC GCCGTGCGAT GCACCCTCCC TATCCGCCAC GTGCGCAGCC TCCAACCCAG    960
CGCGCGGGTC CGACTCCCGG ACCTCGTCCA TCTCGCCGAG GTGGGCCGGT GGCGGTGGTT   1020
CAGCCTCCCC CGCCCCGTGT TCCAGCGCAT GCTGTCCTAC TGCAAGACCC TGAGCCCCGA   1080
CGCGTACTAC AGCGAGCGCG TGTTCAAGTT CAAGAACGCC CTGTGCCACA GCATCACGCT   1140
```

-continued

| | | | | | | |
|---|---|---|---|---|---|---|
| CGCGGGCAAT | GTGCTGCAAG | AGGGGTGGAA | GGGCACGTGC | GCCGAGGAAG | ACGCGCTGTG | 1200 |
| CGCATACGTA | GCCTTCCGCG | CGTGGCAGTC | TAACGCCAGG | TTGGCGGGGA | TTATGAAAGG | 1260 |
| CGCGAAGCGC | TGCGCCGCCG | ACTCTTTGAG | CGTGGCCGGC | TGGCTGGACA | CCATTTGGGA | 1320 |
| CGCCATTAAG | CGGTTCCTCG | GTAGCGTGCC | CCTCGCCGAG | CGCATGGAGG | AGTGGGAACA | 1380 |
| GGACGCCGCG | GTCGCCGCCT | TCGACCGCGG | CCCCCTCGAG | GACGGCGGGC | GCCACTTGGA | 1440 |
| CACCGTGCAA | CCCCCAAAAT | CGCCGCCCCG | CCCTGAGATC | GCCGCGACCT | GGATCGTCCA | 1500 |
| CGCAGCCAGC | GAAGACCGCC | ATTGCGCGTG | CGCTCCCCGC | TGCGACGTCC | CGCGCGAACG | 1560 |
| TCCTTCCGCG | CCCGCCGGCC | AGCCGGATGA | CGAGGCGCTC | ATCCCGCCGT | GGCTGTTCGC | 1620 |
| CGAGCGCCGT | GCCCTCCGCT | GCCGCGAGTG | GGATTTCGAG | GCTCTCCGCG | CGCGCGCCGA | 1680 |
| TACGGCGGCC | GCGCCCGCCC | CGCCGGCTCC | ACGCCCCGCG | CGGTACCCCA | CCGTGCTCTA | 1740 |
| CCGCCACCCC | GCCCACCACG | GCCCGTGGCT | CACCCTTGAC | GAGCCGGGCG | AGGCTGACGC | 1800 |
| GGCCCTGGTC | TTATGCGACC | CACTTGGCCA | GCCGCTCCGG | GGCCCTGAAC | GCCACTTCGC | 1860 |
| CGCCGGCGCG | CATATGTGCG | CGCAGGCGCG | GGGGCTCCAG | GCTTTTGTCC | GTGTCGTGCC | 1920 |
| TCCACCCGAG | CGCCCCTGGG | CCGACGGGGG | CGCCAGAGCG | TGGGCGAAGT | TCTTCCGCGG | 1980 |
| CTGCGCCTGG | GCGCAGCGCT | TGCTCGGCGA | GCCAGCAGTT | ATGCACCTCC | CATACACCGA | 2040 |
| TGGCGACGTG | CCACAGCTGA | TCGCACTGGC | TTTGCGCACG | CTGGCCCAAC | AGGGGGCCGC | 2100 |
| CTTGGCACTC | TCGGTGCGTG | ACCTGCCCGG | GGGTGCAGCG | TTCGACGCAA | ACGCGGTCAC | 2160 |
| CGCCGCCGTG | CGCGCTGGCC | CCCGCCAGTC | CGCGGCCGCG | TCACCGCCAC | CCGGCGACCC | 2220 |
| CCCGCCGCCG | CGCCGCGCAC | GGCGATCGCA | ACGGCACTCG | GACGCTCGCG | GCACTCCGCC | 2280 |
| CCCCGCGCCT | GCGCGCGACC | CGCCGCCGCC | CGCCCCCAGC | CCGCCCGCGC | CACCCCGCGC | 2340 |
| TGGTGACCCG | GTCCCTCCCA | TTCCCGCGGG | GCCGGCGGAT | CGCGCGCGTG | ACGCCGAGCT | 2400 |
| GGAGGTCGCC | TGCGAGCCGA | GCGGCCCCCC | CACGTCAACC | AGGGCAGACC | CAGACAGCGA | 2460 |
| CATCGTTGAA | AGTTACGCCC | GCGCCGCCGG | ACCCGTGCAC | CTCCGAGTCC | GCGACATCAT | 2520 |
| GGACCCACCG | CCCGGCTGCA | AGGTCGTGGT | CAACGCCGCC | AACGAGGGGC | TACTGGCCGG | 2580 |
| CTCTGGCGTG | TGCGGTGCCA | TCTTTGCCAA | CGCCACGGCG | GCCCTCGCTG | CAAACTGCCG | 2640 |
| GCGCCTCGCC | CCATGCCCCA | CCGGCGAGGC | AGTGGCGACA | CCCGGCCACG | GCTGCGGGTA | 2700 |
| CACCCACATC | ATCCACGCCG | TCGCGCCGCG | GCGTCCTCGG | GACCCCGCCG | CCCTCGAGGA | 2760 |
| GGGCGAAGCG | CTGCTCGAGC | GCGCCTACCG | CAGCATCGTC | GCGCTAGCCG | CCGCGCGTCG | 2820 |
| GTGGGCGTGT | GTCGCGTGCC | CCCTCCTCGG | CGCTGGCGTC | TACGGCTGGT | CTGCTGCGGA | 2880 |
| GTCCCTCCGA | GCCGCGCTCG | CGGCTACGCG | CACCGAGCCC | GTCGAGCGCG | TGAGCCTGCA | 2940 |
| CATCTGCCAC | CCCGACCGCG | CCACGCTGAC | GCACGCCTCC | GTGCTCGTCG | GCGCGGGGCT | 3000 |
| CGCTGCCAGG | CGCGTCAGTC | CTCCTCCGAC | CGAGCCCCTC | GCATCTTGCC | CCGCCGGTGA | 3060 |
| CCCGGGCCGA | CCGGCTCAGC | GCAGCGCGTC | GCCCCCAGCG | ACCCCCCTTG | GGGATGCCAC | 3120 |
| CGCGCCCGAG | CCCCGCGGAT | GCCAGGGGTG | CGAACTCTGC | CGGTACACGC | GCGTCACCAA | 3180 |
| TGACCGCGCC | TATGTCAACC | TGTGGCTCGA | GCGCGACCGC | GGCGCCACCA | GCTGGGCCAT | 3240 |
| GCGCATTCCC | GAGGTGGTTG | TCTACGGGCC | GGAGCACCTC | GCCACGCATT | TTCCATTAAA | 3300 |
| CCACTACAGT | GTGCTCAAGC | CCGCGGAGGT | CAGGCCCCCG | CGAGGCATGT | GCGGGAGTGA | 3360 |
| CATGTGGCGC | TGCCGCGGCT | GGCATGGCAT | GCCGCAGGTG | CGGTGCACCC | CCTCCAACGC | 3420 |
| TCACGCCGCC | CTGTGCCGCA | CAGGCGTGCC | CCCTCGGGCG | AGCACGCGAG | GCGGCGAGCT | 3480 |
| AGACCCAAAC | ACCTGCTGGC | TCCGCGCCGC | CGCCAACGTT | GCGCAGGCTG | CGCGCGCCTG | 3540 |

-continued

| | | | | | | |
|---|---|---|---|---|---|---|
| CGGCGCCTAC | ACGAGTGCCG | GGTGCCCCAA | GTGCGCCTAC | GGCCGCGCCC | TGAGCGAAGC | 3600 |
| CCGCACTCAT | GAGGACTTCG | CCGCGCTGAG | CCAGCGGTGG | AGCGCGAGCC | ACGCCGATGC | 3660 |
| CTCCCCTGAC | GGCACCGGAG | ATCCCCTCGA | CCCCCTGATG | GAGACCGTGG | GATGCGCCTG | 3720 |
| TTCGCGCGTG | TGGGTCGGCT | CCGAGCATGA | GGCCCCGCCC | GACCACCTCC | TGGTGTCCCT | 3780 |
| TCACCGTGCC | CCAAATGGTC | CGTGGGGCGT | AGTGCTCGAG | GTGCGTGCGC | GCCCCGAGGG | 3840 |
| GGGCAACCCC | ACCGGCCACT | TCGTCTGCGC | GGTCGGCGGC | GGCCCACGCC | GCGTCTCGGA | 3900 |
| CCGCCCCCAC | CTCTGGCTTG | CGGTCCCCCT | GTCTCGGGGC | GGTGGCACCT | GTGCCGCGAC | 3960 |
| CGACGAGGGG | CTGGCCCAGG | CGTACTACGA | CGACCTCGAG | GTGCGCCGCC | TCGGGGATGA | 4020 |
| CGCCATGGCC | CGGGCGGCCC | TCGCATCAGT | CCAACGCCCT | CGCAAAGGCC | CTTACAATAT | 4080 |
| CAGGGTATGG | AACATGGCCG | CAGGCGCTGG | CAAGACTACC | CGCATCCTCG | CTGCCTTCAC | 4140 |
| GCGCGAAGAC | CTTTACGTCT | GCCCCACCAA | TGCGCTCCTG | CACGAGATCC | AGGCCAAACT | 4200 |
| CCGCGCGCGC | GATATCGACA | TCAAGAACGC | CGCCACCTAC | GAGCGCCGGC | TGACGAAACC | 4260 |
| GCTCGCCGCC | TACCGCCGCA | TCTACATCGA | TGAGGCGTTC | ACTCTCGGCG | GCGAGTACTG | 4320 |
| CGCGTTCGTT | GCCAGCCAAA | CCACCGCGGA | GGTGATCTGC | GTCGGTGATC | GGGACCAGTG | 4380 |
| CGGCCCACAC | TACGCCAATA | ACTGCCGCAC | CCCCGTCCCT | GACCGCTGGC | CTACCGAGCG | 4440 |
| CTCGCGCCAC | ACTTGGCGCT | TCCCCGACTG | CTGGGCGGCC | CGCCTGCGCG | CGGGGCTCGA | 4500 |
| TTATGACATC | GAGGGCGAGC | GCACCGGCAC | CTTCGCCTGC | AACCTTTGGG | ACGGCCGCCA | 4560 |
| GGTCGACCTT | CACCTCGCCT | TCTCGCGCGA | AACCGTGCGC | CGCCTTCACG | AGGCTGGCAT | 4620 |
| ACGCGCATAC | ACCGTGCGCG | AGGCCCAGGG | TATGAGCGTC | GGCACCGCCT | GCATCCATGT | 4680 |
| AGGCAGAGAC | GGCACGGACG | TTGCCCTGGC | GCTGACACGC | GACCTCGCCA | TCGTCAGCCT | 4740 |
| GACCCGGGCC | TCCGACGCAC | TCTACCTCCA | CGAGCTCGAG | GACGGCTCAC | TGCGCGCTGC | 4800 |
| GGGGCTCAGC | GCGTTCCTCG | ACGCCGGGGC | ACTGGCGGAG | CTCAAGGAGG | TTCCCGCTGG | 4860 |
| CATTGACCGC | GTTGTCGCCG | TCGAGCAGGC | ACCACCACCG | TTGCCGCCCG | CCGACGGCAT | 4920 |
| CCCCGAGGCC | CAAGACGTGC | CGCCCTTCTG | CCCCCGCACT | CTGGAGGAGC | TCGTCTTCGG | 4980 |
| CCGTGCCGGC | CACCCCCATT | ACGCGGACCT | CAACCGCGTG | ACTGAGGGCG | AACGAGAAGT | 5040 |
| GCGGTACATG | CGCATCTCGC | GTCACCTGCT | CAACAAGAAT | CACACCGAGA | TGCCCGGAAC | 5100 |
| GGAACGCGTT | CTCAGTGCCG | TTTCGCCGTG | CGGCTACCGC | GCGGGCGAGG | ATGGGTCGAC | 5160 |
| CCTCCGCACT | GCTGTGGCCC | GCCAGCACCC | GCGCCCTTTT | CGCCAGATCC | CACCCCCGCG | 5220 |
| CGTCACTGCT | GGGGTCGCCC | AGGAGTGGCG | CATGACGTAC | TTGCGGGAAC | GGATCGACCT | 5280 |
| CACTGATGTC | TACACGCAGA | TGGGCGTGGC | CGCGCGGGAG | CTCACCGACC | GCTACGCGCG | 5340 |
| CCGCTATCCT | GAGATCTTCG | CCGGCATGTG | TACCGCCCAG | AGCCTGAGCG | TCCCCGCCTT | 5400 |
| CCTCAAAGCC | ACCTTGAAGT | GCGTAGACGC | CGCCCTCGGC | CCCAGGGACA | CCGAGGACTG | 5460 |
| CCACGCCGCT | CAGGGGAAAG | CCGGCCTTGA | GATCCGGGCG | TGGGCCAAGG | AGTGGGTTCA | 5520 |
| GGTTATGTCC | CCGCATTTCC | GCGCGATCCA | GAAGATCATC | ATGCGCGCCT | TGCGCCCGCA | 5580 |
| ATTCCTTGTG | GCCGCTGGCC | ATACGGAGCC | CGAGGTCGAT | GCGTGGTGGC | AGGCCCATTA | 5640 |
| CACCACCAAC | GCCATCGAGG | TCGACTTCAC | TGAGTTCGAC | ATGAACCAGA | CCCTCGCTAC | 5700 |
| TCGGGACGTC | GAGCTCGAGA | TTAGCGCCGC | TCTCTTGGGC | CTCCCTTGCG | CCGAAGACTA | 5760 |
| CCGCGCGCTC | CGCGCCGGCA | GCTACTGCAC | CCTGCGCGAA | CTGGGCTCCA | CTGAGACCGG | 5820 |
| CTGCGAGCGC | ACAAGCGGCG | AGCCCGCCAC | GCTGCTGCAC | AACACCACCG | TGGCCATGTG | 5880 |
| CATGGCCATG | CGCATGGTCC | CCAAAGGCGT | GCGCTGGGCC | GGGATTTTCC | AGGGTGACGA | 5940 |

-continued

TATGGTCATC TTCCTCCCCG AGGGCGCGCG CAGCGCGGCA CTCAAGTGGA CCCCCGCCGA 6000

GGTGGGCTTG TTTGGCTTCC ACATCCCGGT GAAGCACGTG AGCACCCCTA CCCCCAGCTT 6060

CTGCGGGCAC GTCGGCACCG CGGCCGGCCT CTTCCATGAT GTCATGCACC AGGCGATCAA 6120

GGTGCTTTGC CGCCGTTTCG ACCCAGACGT GCTTGAAGAA CAGCAGGTGG CCCTCCTCGA 6180

CCGCCTCCGG GGGGTCTACG CGGCTCTGCC TGACACCGTT GCCGCCAATG CTGCGTACTA 6240

CGACTACAGC GCGGAGCGCG TCCTCGCTAT CGTGCGCGAA CTTACCGCGT ACGCGCGGGG 6300

GCGCGGCCTC GACCACCCGG CCACCATCGG CGCGCTCGAG GAGATTCAGA CCCCCTACGC 6360

GCGCGCCAAT CTCCACGACG CCGACTAACG CCCCTGTACG TGGGGCCTTT AATCTTACCT 6420

ACTCTAACCA GGTCATCACC CACCGTTGTT TCGCCGCATC TGGTGGGTAC CCAACTTTTG 6480

CCATTCGGGA GAGCCCCAGG GTGCCCGAAT GGCTTCTACT ACCCCCATCA CCATGGAGGA 6540

CCTCCAGAAG GCCCTCGAGG CACAATCCCG CGCCCTGCGC GCGGAACTCG CCGCCGGCGC 6600

CTCGCAGTCG CGCCGGCCGC GGCCGCCGCG ACAGCGCGAC TCCAGCACCT CCGGAGATGA 6660

CTCCGGCCGT GACTCCGGAG GGCCCCGCCG CCGCCGCGGC AACCGGGGCC GTGGCCAGCG 6720

CAGGGACTGG TCCAGGGCCC CGCCCCCCCC GGAGGAGCGG CAAGAAACTC GCTCCCAGAC 6780

TCCGGCCCCG AAGCCATCGC GGGCGCCGCC ACAACAGCCT CAACCCCCGC GCATGCAAAC 6840

CGGGCGTGGG GGCTCTGCCC CGCGCCCCGA GCTGGGGCCA CCGACCAACC CGTTCCAAGC 6900

AGCCGTGGCG CGTGGCCTGC GCCCGCCTCT CCACGACCCT GACACCGAGG CACCCACCGA 6960

GGCCTGCGTG ACCTCGTGGC TTTGGAGCGA GGGCGAAGGC GCGGTCTTTT ACCGCGTCGA 7020

CCTGCATTTC ACCAACCTGG GCACCCCCCC ACTCGACGAG GACGGCCGCT GGGACCCTGC 7080

GCTCATGTAC AACCCTTGCG GGCCCGAGCC GCCCGCTCAC GTCGTCCGCG CGTACAATCA 7140

ACCTGCCGGC GACGTCAGGG GCGTTTGGGG TAAAGGCGAG CGCACCTACG CCGAGCAGGA 7200

CTTCCGCGTC GGCGGCACGC GCTGGCACCG ACTGCTGCGC ATGCCAGTGC GCGGCCTCGA 7260

CGGCGACAGC GCCCCGCTTC CCCCCCACAC CACCGAGCGC ATTGAGACCC GCTCGGCGCG 7320

CCATCCTTGG CGCATCCGCT TCGGTGCCCC CCAGGCCTTC CTTGCCGGGC TCTTGCTCGC 7380

CACGGTCGCC GTTGGCACCG CGCGCGCCGG GCTCCAGCCC CGCGCTGATA TGGCGGCACC 7440

TCCTACGCTG CCGCAGCCCC CCTGTGCGCA CGGGCAGCAT TACGGCCACC ACCACCATCA 7500

GCTGCCGTTC CTCGGGCACG ACGGCCATCA TGGCGGCACC TTGCGCGTCG GCCAGCATTA 7560

CCGAAACGCC AGCGACGTGC TGCCCGGCCA CTGGCTCCAA GGCGGCTGGG GTTGCTACAA 7620

CCTGAGCGAC TGGCACCAGG GCACTCATGT CTGTCATACC AAGCACATGG ACTTCTGGTG 7680

TGTGGAGCAC GACCGACCGC CGCCCGCGAC CCCGACGCCT CTCACCACCG CGGCGAACTC 7740

CACGACCGCC GCCACCCCCG CCACTGCGCC GGCCCCCTGC CACGCCGGCC TCAATGACAG 7800

CTGCGGCGGC TTCTTGTCTG GGTGCGGGCC GATGCGCCTG CGCCACGGCG CTGACACCCG 7860

GTGCGGTCGG TTGATCTGCG GGCTGTCCAC CACCGCCCAG TACCCGCCTA CCCGGTTTGG 7920

CTGCGCTATG CGGTGGGGCC TTCCCCCCTG GGAACTGGTC GTCCTTACCG CCCGCCCCGA 7980

AGACGGCTGG ACTTGCCGCG GCGTGCCCGC CCATCCAGGC GCCCGCTGCC CCGAACTGGT 8040

GAGCCCCATG GGACGCGCGA CTTGCTCCCC AGCCTCGGCC CTCTGGCTCG CCACAGCGAA 8100

CGCGCTGTCT CTTGATCACG CCCTCGCGGC CTTCGTCCTG CTGGTCCCGT GGGTCCTGAT 8160

ATTTATGGTG TGCCGCCGCG CCTGTCGCCG CCGCGGCGCC GCCGCCGCCC TCACCGCGGT 8220

CGTCCTGCAG GGGTACAACC CCCCCGCCTA TGGCGAGGAG GCTTTCACCT ACCTCTGCAC 8280

TGCACCGGGG TGCGCCACTC AAGCACCTGT CCCCGTGCGC CTCGCTGGCG TCCGTTTTGA 8340

-continued

| | | | | | | |
|---|---|---|---|---|---|---|
| GTCCAAGATT | GTGGACGGCG | GCTGCTTTGC | CCCATGGGAC | CTCGAGGCCA | CTGGAGCCTG | 8400 |
| CATTTGCGAG | ATCCCCACTG | ATGTCTCGTG | CGAGGGCTTG | GGGGCCTGGG | TACCCGCAGC | 8460 |
| CCCTTGCGCG | CGCATCTGGA | ATGGCACACA | GCGCGCGTGC | ACCTTCTGGG | CTGTCAACGC | 8520 |
| CTACTCCTCT | GGCGGGTACG | CGCAGCTGGC | CTCTTACTTC | AACCCTGGCG | GCAGCTACTA | 8580 |
| CAAGCAGTAC | CACCCTACCG | CGTGCGAGGT | TGAACCTGCC | TTCGGACACA | GCGACGCGGC | 8640 |
| CTGCTGGGGC | TTCCCCACCG | ACACCGTGAT | GAGCGTGTTC | GCCCTTGCTA | GCTACGTCCA | 8700 |
| GCACCCTCAC | AAGACCGTCC | GGGTCAAGTT | CCATACAGAG | ACCAGGACCG | TCTGGCAACT | 8760 |
| CTCCGTTGCC | GGCGTGTCGT | GCAACGTCAC | CACTGAACAC | CCGTTCTGCA | ACACGCCGCA | 8820 |
| CGGACAACTC | GAGGTCCAGG | TCCCGCCCGA | CCCCGGGGAC | CTGGTTGAGT | ACATTATGAA | 8880 |
| TTACACCGGC | AATCAGCAGT | CCCGGTGGGG | CCTCGGGAGC | CCGAATTGCC | ACGGCCCCGA | 8940 |
| TTGGGCCTCC | CCGGTTTGCC | AACGCCATTC | CCCTGACTGC | TCGCGGCTTG | TGGGGGCCAC | 9000 |
| GCCAGAGCGC | CCCCGGCTGC | GCCTGGTCGA | CGCCGACGAC | CCCCTGCTGC | GCACTGCCCC | 9060 |
| TGGACCCGGC | GAGGTGTGGG | TCACGCCTGT | CATAGGCTCT | CAGGCGCGCA | AGTGCGGACT | 9120 |
| CCACATACGC | GCTGGACCGT | ACGGCCATGC | TACCGTCGAA | ATGCCCGAGT | GGATCCACGC | 9180 |
| CCACACCACC | AGCGACCCCT | GGCATCCACC | GGGCCCCTTG | GGGCTGAAGT | TCAAGACAGT | 9240 |
| TCGCCCGGTG | GCCCTGCCAC | GCACGTTAGC | GCCACCCCGC | AATGTGCGTG | TGACCGGGTG | 9300 |
| CTACCAGTGC | GGTACCCCCG | CGCTGGTGGA | AGGCCTTGCC | CCCGGGGGAG | GCAATTGCCA | 9360 |
| TCTCACCGTC | AATGGCGAGG | ACCTCGGCGC | CGTCCCCCCT | GGGAAGTTCG | TCACCGCCGC | 9420 |
| CCTCCTCAAC | ACCCCCCCGC | CCTACCAAGT | CAGCTGCGGG | GGCGAGAGCG | ATCGCGCGAC | 9480 |
| CGCGCGGGTC | ATCGACCCCG | CCGCGCAATC | GTTTACCGGC | GTGGTGTATG | GCACACACAC | 9540 |
| CACTGCTGTG | TCGGAGACCC | GGCAGACCTG | GGCGGAGTGG | GCTGCTGCCC | ATTGGTGGCA | 9600 |
| GCTCACTCTG | GGCGCCATTT | GCGCCCTCCC | ACTCGCTGGC | TTACTCGCTT | GCTGTGCCAA | 9660 |
| ATGCTTGTAC | TACTTGCGCG | GCGCTATAGC | GCCTCGCTAG | TGGGCCCCCG | CGCGAAACCC | 9720 |
| GCACTAGGCC | ACTAGATCCC | CGCACCTGTT | GCTGTATAG | | | 9759 |

( 2 ) INFORMATION FOR SEQ ID NO:2:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

TGGTCTCTTA CCCAACT 17

( 2 ) INFORMATION FOR SEQ ID NO:3:

( i ) SEQUENCE CHARACTERISTICS:
( A ) LENGTH: 49 base pairs
( B ) TYPE: nucleic acid
( C ) STRANDEDNESS: double
( D ) TOPOLOGY: linear ( i i ) MOLECULE TYPE: DNA (genomic)

-continued ( i i i ) HYPOTHETICAL: NO ( i v ) ANTI-SENSE: NO ( v ) FRAGMENT TYPE: N-terminal ( i x ) FEATURE:
( A ) NAME/KEY: misc_feature
( B ) LOCATION: 5..10
( D ) OTHER INFORMATION: /note= "SpeI site"

( i x ) FEATURE:
( A ) NAME/KEY: misc_feature
( B ) LOCATION: 13..18
( D ) OTHER INFORMATION: /note= "HindIII site"

( x i ) SEQUENCE DESCRIPTION: SEQ ID NO:3:

AGCTACTAGT CTAAGCTTTC GGACCTCGCT TAGGACTCCC ATTCCCATG 49

( 2 ) INFORMATION FOR SEQ ID NO:4:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

TTCGAAGCTT ATTTAGGTCA CACTATAGCA TGGAAGCTAT CGGACCTC 48

( 2 ) INFORMATION FOR SEQ ID NO:5:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

TGGTCTCTTA CCCAACTAAA A 21

( 2 ) INFORMATION FOR SEQ ID NO:6:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

-continued

GATGCATCCC TATAGTGAGT CGTATTAG 28

( 2 ) INFORMATION FOR SEQ ID NO:7:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

AATTCTAATA CAACTCACTA TAGGGATGCA TCTGCA 36

( 2 ) INFORMATION FOR SEQ ID NO:8:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

AATGCCCGAG TGGATCCA 18

( 2 ) INFORMATION FOR SEQ ID NO:9:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

ACGTGCATGC CTGCAGTTTT TTTTTTTTTT TTTTTT 36

( 2 ) INFORMATION FOR SEQ ID NO:10:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO

-continued ( v ) FRAGMENT TYPE: N-terminal ( i x ) FEATURE:
( A ) NAME/KEY: misc_feature
( B ) LOCATION: 1..6
( D ) OTHER INFORMATION: /note= "HindIII site"

( i x ) FEATURE:
( A ) NAME/KEY: promoter
( B ) LOCATION: 7..23

( x i ) SEQUENCE DESCRIPTION: SEQ ID NO:10:

AAGCTTATTT AGGTGACACT ATAGCATGGA AGCTATCGGA CCTCGCTT 48

( 2 ) INFORMATION FOR SEQ ID NO:11:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: N-terminal ( i x ) FEATURE:
( A ) NAME/KEY: misc_feature
( B ) LOCATION: 1..6
( D ) OTHER INFORMATION: /note= "HindIII site"

( i x ) FEATURE:
( A ) NAME/KEY: promoter
( B ) LOCATION: 7..23

( x i ) SEQUENCE DESCRIPTION: SEQ ID NO:11:

AAGCTTATTT AGGTGACACT ATAGCAATGG AAGCTATCGG ACCTCGCTT 49